United States Patent
Li et al.

(10) Patent No.: US 11,813,594 B2
(45) Date of Patent: Nov. 14, 2023

(54) HETEROGENEOUS CATALYSTS FOR SUBSTRATE-DIRECTED HYDROGENATION AND METHODS OF PRODUCING SUCH CATALYSTS

(71) Applicant: Purdue Research Foundation, West Lafayette, IN (US)

(72) Inventors: Christina W. Li, Lafayette, IN (US); Alexander J. Shumski, Bethel Park, PA (US); William A. Swann, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/572,909

(22) Filed: Jan. 11, 2022

(65) Prior Publication Data

US 2022/0219150 A1 Jul. 14, 2022

Related U.S. Application Data

(60) Provisional application No. 63/135,777, filed on Jan. 11, 2021.

(51) Int. Cl.
*B01J 21/04* (2006.01)
*B01J 21/08* (2006.01)
(Continued)

(52) U.S. Cl.
CPC ......... *B01J 23/8926* (2013.01); *B01J 23/892* (2013.01); *B01J 23/8913* (2013.01);
(Continued)

(58) Field of Classification Search
CPC ... B01J 21/04; B01J 21/08; B01J 23/42; B01J 23/44; B01J 23/464; B01J 23/60;
(Continued)

(56) References Cited

U.S. PATENT DOCUMENTS

| 8,664,147 B2 * | 3/2014 | Bello | B01J 35/0013 |
| | | | 423/247 |
| 8,703,639 B2 * | 4/2014 | Wan | B01J 35/10 |
| | | | 502/185 |

(Continued)

OTHER PUBLICATIONS

Crabtree, R.H. et al., "Directing Effects in Homogeneous Hydrogenation with [Ir(cod)(PCy3)(py)]PF6", Chemistry Department", Yale University, New Haven, Connecticut 06511, Received Feb. 20, 1986, J. Org. Chem. 1986, pp. 2655-2661.

(Continued)

*Primary Examiner* — Cam N. Nguyen
(74) *Attorney, Agent, or Firm* — Hartman Global IP Law; Gary M. Hartman; Domenica N.S. Hartman

(57) ABSTRACT

A heterogeneous catalyst for substrate-directed hydrogenation includes bimetallic nanoparticles of $M_1$-$M_2$, wherein $M_1$ is a noble metal and $M_2$ is a first-row transition metal. The bimetallic nanoparticles are on a substrate and atoms of both the noble metal and the first-row transition metal are distributed across surfaces of the bimetallic nanoparticles. The heterogeneous catalyst may be produced by providing $M_1$-$M_2$ bimetallic nanoparticles on a substrate to produce an intermediate composition, and performing a reduction process on the intermediate composition such that atoms of both the noble metal ($M_1$) and the first-row transition metal ($M_2$) are distributed across surfaces of the bimetallic nanoparticles and thereby form the heterogeneous catalyst. The catalyst may be used for performing directed hydrogenation of a substrate.

20 Claims, 14 Drawing Sheets

(51) Int. Cl.
| | |
|---|---|
| B01J 23/42 | (2006.01) |
| B01J 23/44 | (2006.01) |
| B01J 23/46 | (2006.01) |
| B01J 23/60 | (2006.01) |
| B01J 23/72 | (2006.01) |
| B01J 23/745 | (2006.01) |
| B01J 23/75 | (2006.01) |
| B01J 23/755 | (2006.01) |
| B01J 23/89 | (2006.01) |
| B01J 35/00 | (2006.01) |
| B01J 37/02 | (2006.01) |
| B01J 37/08 | (2006.01) |
| C07C 29/17 | (2006.01) |

(52) U.S. Cl.
CPC ......... B01J 35/006 (2013.01); B01J 37/0201 (2013.01); B01J 37/08 (2013.01); C07C 29/172 (2013.01); *B01J 21/04* (2013.01); *B01J 21/08* (2013.01); *C07B 2200/07* (2013.01)

(58) Field of Classification Search
CPC . B01J 23/72; B01J 23/745; B01J 23/75; B01J 23/755; B01J 23/8906; B01J 23/8913; B01J 23/892; B01J 23/8926; B01J 35/006; B01J 37/0201
USPC ............... 502/258–262, 327–328, 332–339, 502/345–346, 355, 415, 439
See application file for complete search history.

(56) References Cited

U.S. PATENT DOCUMENTS

| | | | | |
|---|---|---|---|---|
| 8,741,801 | B2* | 6/2014 | Fang | B01J 23/8913 |
| | | | | 977/773 |
| 9,017,576 | B2* | 4/2015 | Biausque | C01B 3/26 |
| | | | | 502/262 |
| 9,095,844 | B2* | 8/2015 | Chung | B01J 37/18 |
| 9,246,177 | B2* | 1/2016 | Stamenkovic | H01M 4/921 |
| 9,283,545 | B2* | 3/2016 | Asefa | B01J 23/74 |
| 9,469,535 | B2* | 10/2016 | Biausque | C01B 3/40 |
| 9,680,161 | B2* | 6/2017 | Yang | C22F 1/14 |
| 9,694,351 | B1* | 7/2017 | Roy | B01J 37/16 |
| 9,972,731 | B2* | 5/2018 | Yoon | H01L 31/1864 |
| 10,183,276 | B2* | 1/2019 | Karpov | B01D 53/945 |
| 10,486,141 | B2* | 11/2019 | Vardon | B01J 23/8913 |
| 10,493,437 | B2* | 12/2019 | Maclachlan | B01J 37/0201 |
| 10,537,881 | B2* | 1/2020 | Li | B01J 37/18 |
| 10,686,195 | B2* | 6/2020 | Yang | H01M 4/8657 |
| 10,821,422 | B2* | 11/2020 | Chaudhari | B01J 37/0236 |
| 10,913,052 | B1* | 2/2021 | Li | C07C 5/09 |
| 10,960,470 | B2* | 3/2021 | Humphrey | C22C 1/047 |
| 10,967,363 | B1* | 4/2021 | Li | B01J 27/24 |
| 11,285,463 | B1* | 3/2022 | Zoican-Loebick | C01B 3/386 |
| 11,351,521 | B2* | 6/2022 | Gong | B01J 29/0333 |
| 11,478,780 | B2* | 10/2022 | Herzfeld | B22F 9/24 |
| 11,524,279 | B1* | 12/2022 | Li | B01J 21/063 |
| 2016/0204449 | A1* | 7/2016 | Mal | C22C 5/04 |
| | | | | 429/524 |
| 2017/0128917 | A1* | 5/2017 | Hunt | H01M 4/925 |
| 2018/0311651 | A1* | 11/2018 | Ravon | B01J 37/0018 |
| 2019/0168190 | A1* | 6/2019 | Vardon | B01J 23/6567 |
| 2020/0024295 | A1* | 1/2020 | Muresan | C07F 15/045 |
| 2020/0122122 | A1* | 4/2020 | Gong | B01J 37/08 |
| 2021/0252494 | A1* | 8/2021 | Ding | B01J 37/0063 |
| 2022/0184585 | A1* | 6/2022 | Griffin | B01J 23/755 |

OTHER PUBLICATIONS

Crabtree, R.H. et al., "Occurrence and Origin of a Pronounced Directing Effect of a Hydroxyl Group in Hydrogenation with [Ir(cod)P-c-Hx3(py)]PF6", Organometallics 1983, 2, pp. 681-682.
Evans, D.A. et al., "Rhodium (I)-Catalyzed Hydrogenation of Olefins. The Documentation of Hydroxyl-Directed Stereochemical Control in Cyclic and Acyclic Systems", J. Am. Chem. Soc. 1984, 106, pp. 3866-3868.
Friedfeld, M.R. et al., "Bis(phosphine)cobalt Dialkyl Complexes for Directed Catalytic Alkene Hydrogenation", ACS Publications, 2014, pp. 13178-13181.
Mitsui, S. et. al., "The Stereoselectivity of Catalysts in Hydrogenation. I. The Catalytic Hydrogenation of 2-Cyclopentylidenecyclopentanol and 2-Benzylidene-1-tetralol", Bulletin of the Chemical Society of Japan, vol. 39, 1966, pp. 694-697.
Ranade, V.S. et al., "Functional-Group-Directed Diastereoselective Hydrogenation of Aromatic Compounds. 2", J. Org. Chem. 2000, 65, pp. 1132-1138.
Ranade, V.S. et al., "Functional-Group-Directed Diastereoselective Hydrogenation of Aromatic Compounds. 1", J. Org. Chem. 1999, 64, pp. 8862-8867.
Sehgal, R.K. et al., "The Effect of Ring Size on Hydrogenation of Cyclic Allylic Alcohols", J. Org. Chem., vol. 40, No. 21, 1975, pp. 3073-3078.
Stork, G. et al., "Stereocontrol in Homogeneous Catalytic Hydrogenation via Hydroxyl Coordination," J. Am. Chem. Soc. 1983, 108, pp. 1072-1073.
Thompson, H.W. et al., "Stereochemical Control of Reductions. III. An Approach to Group Haptophilicities," Journal of the American Chemical Society, 95:19, 1973, pp. 6379-6386.
Thompson, H.W. et al., "Stereochemical Control of Reductions. 8 1. Exploration of the Inner Limits of the Haptophilic Effect with 2-Exo-Substituted 7-Methylenenorbornanes2," J. Org. Chem. 1985, 50, pp. 4270-4276.
Thompson, H .W., "Stereochemical Control of Reductions. The Directive Effect of Carbomethoxy vs. Hydroxymethyl Groups in Catalytic Hydrogenation," The Journal of Organic Chemistry, vol. 36, No. 18, 1971, pp. 2577-2581.
Thompson, H.W. et al., "Stereochemical Control of Reductions. 5 1. Effects of Electron Density and Solvent on Group Haptophilicity 2," J. Org. Chem., vol. 41, No. 17, 1976, pp. 2903-2906.

* cited by examiner

Table 1. Screening of Supported Pd-M Catalysts[a]

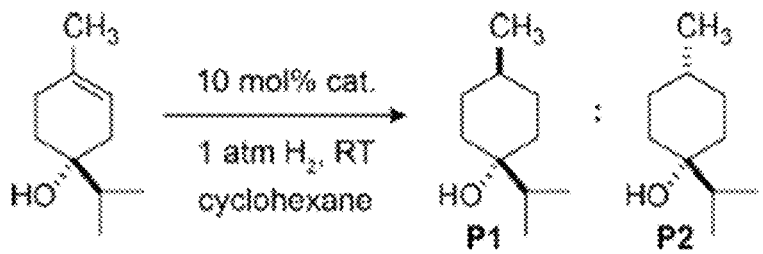

| Entry | Catalyst | Time | Conversion[b] | dr (P1:P2)[b] |
|---|---|---|---|---|
| 1 | Pd/Al$_2$O$_3$ | 2 h | 99% | 1:1 |
| 2 | Pd$_3$Fe/Al$_2$O$_3$ | 2 h | 90% | 2:1 |
| 3 | Pd$_3$Co/Al$_2$O$_3$ | 2 h | 99% | 2:1 |
| 4 | Pd$_3$Ni/Al$_2$O$_3$ | 2 h | 99% | 3:1 |
| 5 | Pd$_3$Cu/Al$_2$O$_3$ | 2 h | 43% | 5:1 |
| 6 | Pd$_3$Zn/Al$_2$O$_3$ | 2 h | 56% | 4:1 |
| Pd$_3$Cu/SiO$_2$ | | | | |
| 7 | RT H$_2$ | 20 h | 99% | 1:1 |
| 8 | 600H$_2$ | 20 h | 95% | 2:1 |
| 9 | 800H$_2$ | 20 h | 99% | 3:1 |
| 10 | 600N$_2$ | 20 h | 98% | 3:1 |
| 11 | 700N$_2$ | 20 h | 66% | 10:1 |
| 12 | 800N$_2$ | 20 h | 30% | 17:1 |
| 13 | 600N$_2$-400H$_2$ | 20 h | 99% | 3:1 |
| 14 | 700N$_2$-400H$_2$ | 20 h | 95% | 8:1 |
| 15 | 800N$_2$-400H$_2$ | 20 h | 99% | 16:1 |
| 16 | 800N$_2$-800H$_2$ | 20 h | 99% | 6:1 |

[a]0.1 mmol substrate, 50 mg 2 wt % Pd-M catalyst, 5 mL cyclohexane, H$_2$ balloon. [b]Single run conversions and diastereomeric ratios (dr) determined by GC with decane as an internal standard.

FIG. 2

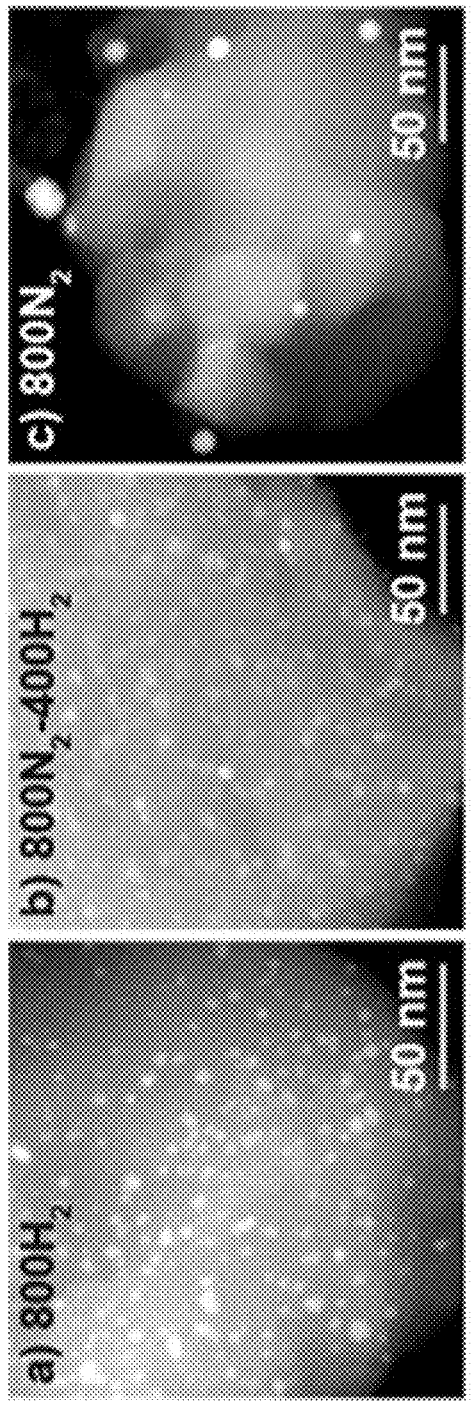
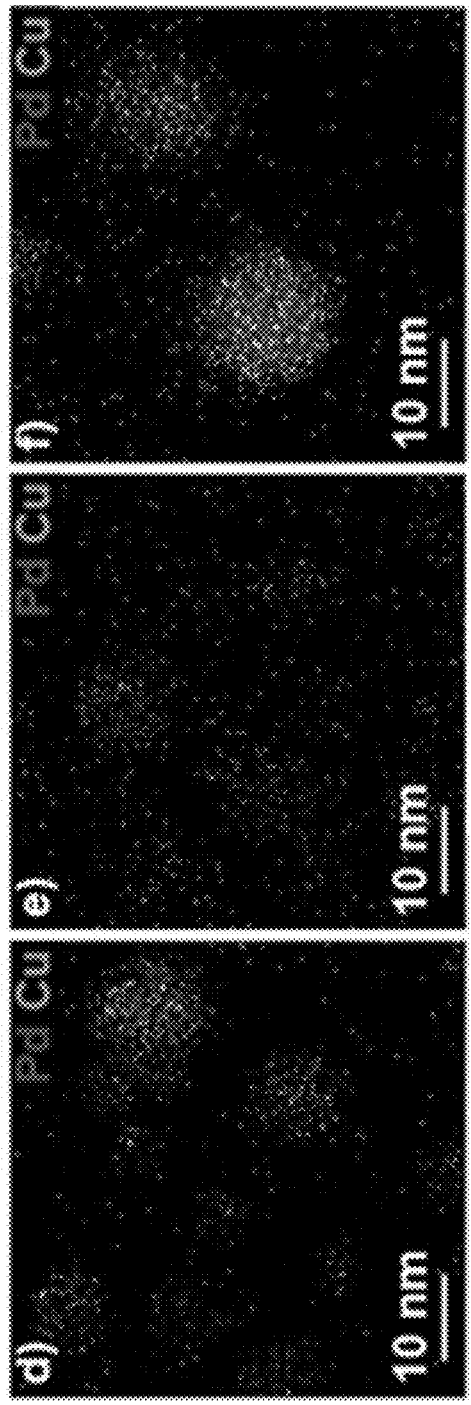
FIG. 4A  FIG. 4B  FIG. 4C
FIG. 4D  FIG. 4E  FIG. 4F

Table 2. Pd and Cu K-edge XAS Fitting Parameters for Thermally Treated Pd$_3$Cu/SiO$_2$ Catalysts

| sample | edge | scattering pair | CN | R (Å) | $\sigma^2$ (Å)$^a$ | $E_0$ (eV)$^a$ |
|---|---|---|---|---|---|---|
| Pd$_3$Cu/SiO$_2$ 800 °C H$_2$ | Pd | Pd–Pd | 7.0 ± 0.6 | 2.717 ± 0.005 | 0.005 | −3.0 ± 0.6 |
|  |  | Pd–Cu | 1.6 ± 0.6 |  |  |  |
|  | Cu | Cu–O | 1.9 ± 0.4 | 1.917 ± 0.018 | 0.009 | −3.4 ± 0.7 |
|  |  | Cu–Pd | 4.8 ± 0.5 | 2.680 ± 0.008 |  |  |
| Pd$_3$Cu/SiO$_2$ 800 °C N$_2$ + 400 °C H$_2$ | Pd | Pd–Pd | 9.8 ± 0.4 | 2.728 ± 0.002 | 0.005 | −6.3 ± 0.3 |
|  |  | Pd–Cu | 1.4 ± 0.4 |  |  |  |
|  | Cu | Cu–O | 3.0 ± 0.3 | 1.924 ± 0.007 | 0.009 | −2.3 ± 0.4 |
|  |  | Cu–Pd | 3.9 ± 0.3 | 2.725 ± 0.006 |  |  |
| Pd$_3$Cu/SiO$_2$ 800 °C N$_2$ | Pd | Pd–O | 1.4 ± 0.4 | 2.041 ± 0.028 | 0.005 | −6.5 ± 0.4 |
|  |  | Pd–Pd | 8.3 ± 0.5 | 2.729 ± 0.003 |  |  |
|  |  | Pd–Cu | 0.8 ± 0.5 |  |  |  |
|  | Cu | Cu–O | 4.1 ± 0.1 | 1.928 ± 0.003 | 0.009 | −3.0 ± 0.3 |
|  |  | Cu–Pd | 1.8 ± 0.2 | 2.710 ± 0.007 |  |  |

$^a\sigma^2$ values are determined based on metal foil references and fixed during the EXAFS fitting.

FIG. 6

Table 3. Diastereoselectivity and Conversion for Three Directing Groups over Pd/SiO$_2$ and Pd$_3$Cu/SiO$_2$ Catalysts

| | dr (P1:P2)[a] at high conversion | | |
|---|---|---|---|
| catalyst | R = OH | R = OMe | R = H |
| Pd/SiO$_2$ | 1:3 | 1:7 | 1:3 |
| Pd$_3$Cu 800H$_2$ | 3:1 | 1:4 | 1:3 |
| Pd$_3$Cu 800N$_2$-400H$_2$ | 16:1 | 1:2 | 1:3 |

| | conversion (%) at fixed time | | |
|---|---|---|---|
| catalyst | R = OH | R = OMe | R = H |
| Pd/SiO$_2$[b] | 99 | 96 | 74 |
| Pd$_3$Cu 800 H$_2$[c] | 31 | 64 | 11 |
| Pd$_3$Cu 800N$_2$-400H$_2$[c] | 21 | 49 | 8 |

[a]Diastereomeric ratios averaged over three runs; standard deviations provided in Table S4. [b]Conversions obtained at 2 h. [c]Conversions obtained at 4 h.

FIG. 8

Table 4. Substrate Scope for Pd₃Cu/SiO₂-Catalyzed Directed Hydrogenation[a]

$$\text{H}_3\text{C}-\overset{R_1}{\underset{R_2}{=}} \xrightarrow[\text{1 atm H}_2,\ \text{RT, 20 h}]{\text{10 mol\% Pd or Pd}_3\text{Cu/SiO}_2} \text{H}_3\text{C}-\overset{R_1}{\underset{R_2}{-}}$$

| entry | alkene | | %conversion* | DR* | %isomerized* |
|---|---|---|---|---|---|
| (1) | | Pd: | 99% | 1:3 dr | <1% |
|  |  | Pd₃Cu: | 99% | 16:1 dr | <1% |
| (2) | | Pd: | 99% | 1:1 dr | <1% |
|  |  | Pd₃Cu: | 71% | 12:1 dr | <1% |
| (3)^ | | Pd: | 99% | 1:1 dr | 9% |
|  |  | Pd₃Cu: | 99% | 24:1 dr | 6% |
| (4)^ | | Pd: | 99% | 2:1 dr | 9% |
|  |  | Pd₃Cu: | 99% | 8:1 dr | 6% |
| (5)^ | | Pd: | 99% | 1:2 dr | 6% |
|  |  | Pd₃Cu: | 97% | 2:1 dr | 5% |
| (6)^ | | Pd: | 99% | 8:1 dr | 6% |
|  |  | Pd₃Cu: | 83% | 22:1 dr | 5% |
| (7) | | Pd: | 99% | 1:2 dr | 2% |
|  |  | Pd₃Cu: | 99% | 1:1 dr | 11% |
| (8) | | Pd: | 99% | 1:1 dr | <1% |
|  |  | Pd₃Cu: | 99% | 4:1 dr | 4% |

[a](*) Conversion, diastereomeric ratio (dr), and percent isomerization determined by GC with decane as an internal standard except for entry 7, where dr is determined by NMR. (^) Entries 3 and 4 and entries 5 and 6 run as a mixture of diastereomers.

FIG. 9

Table 5. Screening of Supported Pt-M Catalysts in Terpinen-4-ol Hydrogenation.

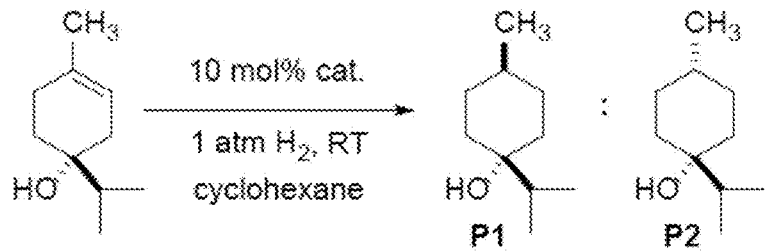

| Catalyst | Time | Conversion | dr (P1:P2) |
|---|---|---|---|
| iwi-Pt/SiO₂ | 18 h | 99% | 1:1 |
| iwi-Pt₃Cu/SiO₂ | 18 h | 99% | 7:1 |
| iwi-PtCu/SiO₂ | 18 h | 99% | 9:1 |
| iwi-PtFe/SiO₂ | 18 h | 99% | 2:1 |
| iwi-PtCo/SiO₂ | 18 h | 99% | 7:1 |
| iwi-PtNi/SiO₂ | 18 h | 99% | 6:1 |
| iwi-PtZn/SiO₂ | 18 h | 99% | 5:1 |
| c-Pt/Al₂O₃ | 6 h | 99% | 2:1 |
| c-Pt₃Cu/Al₂O₃ | 20 h | 99% | 5:1 |
| c-PtCu/Al₂O₃ | 6 h | 99% | 7:1 |
| c-PtCu₃/Al₂O₃ | 6 h | 61% | 13:1 |

*The prefix 'iwi' indicates a catalyst prepared by incipient wetness impregnation.
*The prefix 'c' indicates a catalyst prepared by colloidal synthesis.

FIG. 11

Table 6. Screening of Supported Rh-M Catalysts in Terpinen-4-ol Hydrogenation.

| Catalyst | Time | Conversion | dr (P1:P2) |
|---|---|---|---|
| Rh/SiO$_2$ | 12 h | 94% | 1:1 |
| Rh$_2$Fe/SiO$_2$ | 12 h | 99% | 3:1 |
| Rh$_2$Co/SiO$_2$ | 12 h | 99% | 6:1 |
| Rh$_2$Ni/SiO$_2$ | 12 h | 99% | 9:1 |
| Rh$_2$Cu/SiO$_2$ | 12 h | 34% | 12:1 |
| Rh$_2$Zn/SiO$_2$ | 12 h | 99% | 4:1 |

Table 7. Screening of Supported Rh-M Catalysts in 2-Indanol Hydrogenation.

| Catalyst | Time | Conversion | dr (P1:P2) |
|---|---|---|---|
| Rh/SiO$_2$ | 12 h | 99% | 1:1 |
| Rh$_2$Fe/SiO$_2$ | 12 h | 0% | n/a |
| Rh$_2$Co/SiO$_2$ | 12 h | 61% | 3:1 |
| Rh$_2$Ni/SiO$_2$ | 12 h | 70% | 4:1 |
| Rh$_2$Cu/SiO$_2$ | 12 h | 5% | n/a |
| Rh$_2$Zn/SiO$_2$ | 12 h | 73% | 3:1 |
| Rh$_1$Ni$_1$/SiO$_2$ | 20 h | 84% | 3:1 |
| Rh$_1$Ni$_2$/SiO$_2$ | 20 h | 57% | 5:1 |
| c-RhNi$_2$/C | 20 h | 73% | 3:1 |

HETEROGENEOUS CATALYSTS FOR SUBSTRATE-DIRECTED HYDROGENATION AND METHODS OF PRODUCING SUCH CATALYSTS

CROSS REFERENCE TO RELATED APPLICATIONS

This application claims the benefit of U.S. Provisional Application No. 63/135,777, filed Jan. 11, 2021, the contents of which are incorporated herein by reference.

STATEMENT REGARDING FEDERALLY SPONSORED RESEARCH

This invention was made with government support under Contract No. CHE-2045013 awarded by the National Science Foundation. The government has certain rights in the invention.

BACKGROUND OF THE INVENTION

The present invention generally relates to substrate-directed hydrogenation. The invention particularly relates to heterogeneous catalysts for substrate-directed hydrogenation that include bimetallic nanoparticles of $M_1$-$M_2$, wherein $M_1$ is a noble metal and $M_2$ is a first-row transition metal, and atoms of both the noble metal and the first-row transition metal are distributed across surfaces of the bimetallic nanoparticles.

Substrate-directed hydrogenations, in which product selectivity is dictated by the binding of an ancillary directing group on a substrate to a catalyst, are an important class of selective organic reactions that provide access to highly functionalized and diastereomerically pure products. High selectivity toward directed hydrogenation has been demonstrated using molecular catalysts based on Ir, Rh, and Co, in which an organometallic complex simultaneously activates and coordinates $H_2$, the directing group, and an alkene (olefin) in a well-defined orientation at a single metal center in order to achieve facially selective addition of $H_2$ across the alkene (FIG. 1A). As such, directed hydrogenation is typically catalyzed by homogeneous Rh and Ir complexes. As used herein, homogeneous catalysts dissolve in a solvent that contains an unsaturated substrate and heterogeneous catalysts are solids that are suspended in the solvent containing a dissolved substrate.

Heterogeneous systems based on supported metal nanoparticles tend to be more reactive, robust, and recyclable as hydrogenation catalysts than their molecular counterparts, but no heterogeneous catalyst has been able to achieve equivalently high directivity due to a lack of control over substrate binding orientation at the catalyst surface. In fact, no existing heterogeneous catalyst has shown any significant or general directing capability. A few examples using monometallic heterogeneous catalysts such as Raney Ni and supported Pd, Pt, and Rh nanoparticles have shown a mild directing group effect with alcohol, ether, and amine functionality, but the strength of the interaction between the directing group and the surface is weak compared to homogeneous complexes, resulting in poor diastereoinduction.

In view of the above, it can be appreciated that it would be desirable if a method were available for performing directed hydrogenation with a heterogeneous catalyst that was capable of at least some, and preferably significant, directing capability.

BRIEF DESCRIPTION OF THE INVENTION

The present invention provides heterogeneous catalysts suitable for directed hydrogenation of a substrate and methods for producing the same.

According to one aspect of the invention, a heterogeneous catalyst is provided that is configured for directed hydrogenation of a substrate. The heterogeneous catalyst includes bimetallic nanoparticles of $M_1$-$M_2$, wherein $M_1$ is a noble metal and $M_2$ is a first-row transition metal, the bimetallic nanoparticles are on a supporting material, and atoms of both the noble metal and the first-row transition metal are distributed across surfaces of the bimetallic nanoparticles.

According to another aspect of the invention, a method is provided for producing a heterogeneous catalyst configured for directed hydrogenation of a substrate. The method includes providing bimetallic nanoparticles on a supporting material to produce an intermediate composition, wherein the bimetallic nanoparticles are $M_1$-$M_2$ where $M_1$ is a noble metal and $M_2$ is a first-row transition metal, and performing a reduction process on the intermediate composition such that atoms of both the noble metal and the first-row transition metal are distributed across surfaces of the bimetallic nanoparticles and thereby form the heterogeneous catalyst.

According to another aspect of the invention, a heterogeneous catalyst for directed hydrogenation of an alkene-containing substrate includes Pd-M bimetallic nanoparticles on a supporting material wherein M is Fe, Co, Ni, Cu, or Zn.

According to another aspect of the invention, a heterogeneous catalyst for directed hydrogenation of an alkene-containing substrate includes Pt-M bimetallic nanoparticles on a supporting material wherein M is Fe, Co, Ni, Cu, or Zn.

According to another aspect of the invention, a heterogeneous catalyst for directed hydrogenation of an alkene-containing or arene-containing substrate includes Rh-M bimetallic nanoparticles on a supporting material wherein M is Fe, Co, Ni, Cu, or Zn.

Another aspect of the invention is a method of using a heterogeneous catalyst as described above for performing directed hydrogenation of a substrate.

Technical effects of the heterogeneous catalysts and methods described above preferably include the capability of performing directed hydrogenation with the heterogeneous catalyst with sufficient directing capability such that it may be used as a practical alternative to molecular catalysts.

Other aspects and advantages of this invention will be appreciated from the following detailed description.

BRIEF DESCRIPTION OF THE DRAWINGS

FIG. 2 includes a Table 1 that includes data relating to screening of certain nonlimiting Pd-M heterogeneous catalysts.

FIGS. 4A through 4F include STEM images and EDS maps for $Pd_3Cu/SiO_2$ treated under 800° C. $H_2$ (FIGS. 4A and 4D), 800° C. $N_2$-400° C. $H_2$ (FIGS. 4B and 4E), and 800° C. $N_2$ (FIGS. 4C and 4F).

FIG. 6 includes a Table 2 that includes data relating to Pd and Cu K-edge XAS fitting parameters for thermally treated Pd$_3$Cu/SiO$_2$ heterogeneous catalysts.

FIG. 8 includes a Table 3 that includes data relating to diastereoselectivity and conversion for three directing groups over Pd/SiO$_2$ and Pd$_3$Cu/SiO$_2$ heterogeneous catalysts.

FIG. 9 includes a Table 4 that includes data relating to substrate scope for Pd$_3$Cu/SiO$_2$-catalyzed directed hydrogenation.

FIG. 11 includes a Table 5 that includes data related to screening of Pt-M heterogeneous catalysts for directed hydrogenation of alkene substrates.

DETAILED DESCRIPTION OF THE INVENTION

Figures 1A, 1B:
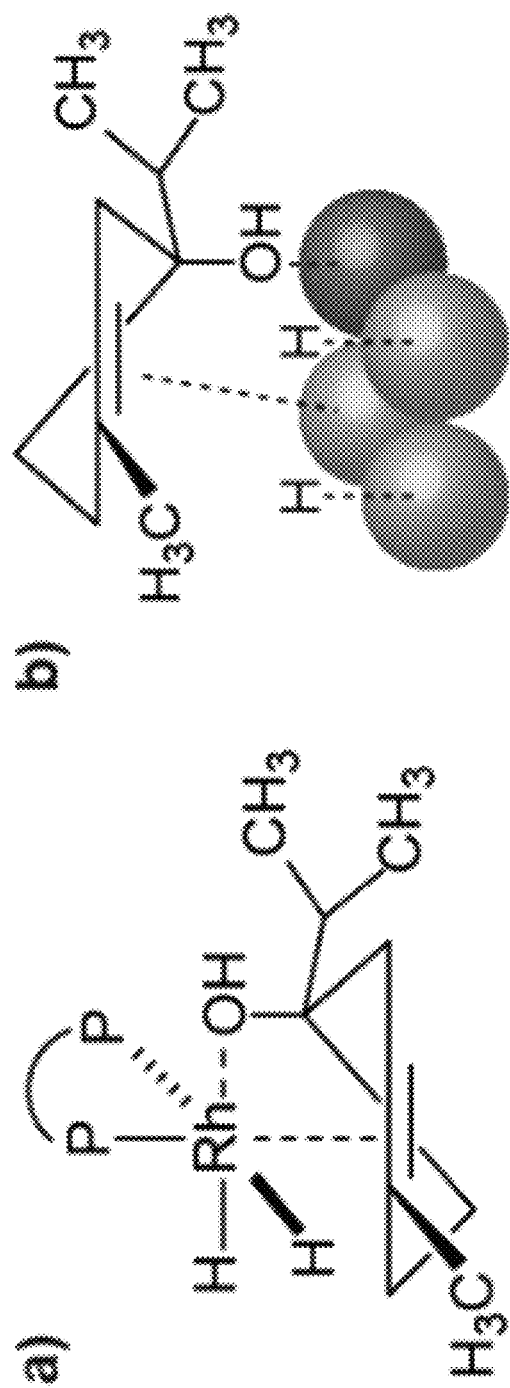
FIGS. 1A and 1B schematically represent homogeneous and heterogeneous directed hydrogenation, respectively.

The intended purpose of the following detailed description of the invention and the phraseology and terminology employed therein is to describe what is shown in the drawings, which include depictions of one or more nonlimiting embodiments of the invention, and to describe certain but not all aspects of what is depicted in the drawings, including the embodiment(s). The following detailed description also describes certain investigations relating to the embodiment(s), and identifies certain but not all alternatives of the embodiment(s). Therefore, the appended claims, and not the detailed description, are intended to particularly point out subject matter regarded as the invention, including certain but not necessarily all of the aspects and alternatives described in the detailed description.

Disclosed herein are heterogeneous catalysts for substrate-directed hydrogenation, methods of producing such heterogeneous catalysts, methods for controlling the diastereoselectivity of such heterogeneous catalysts, and methods for performing directed hydrogenation of substrates with the heterogeneous catalysts. The heterogeneous catalysts include bimetallic nanoparticles of M$_1$-M$_2$, wherein M$_1$ is a noble metal and M$_2$ is a first-row transition metal. The bimetallic nanoparticles are on a support material and atoms of both the noble metal and the first-row transition metal are distributed across surfaces of the bimetallic nanoparticles. Experimental investigations leading to the present invention, discussed below, demonstrated that the heterogeneous catalysts were capable of high conversion and diastereoselectivity in exemplary hydroxyl-directed hydrogenation reactions. It is believed that the alcohol (OH) directing group was adsorbed to the more oxophilic alloying metal (first-row transition metal atom) while the hydrogen bound to adjacent noble metal atoms, thus enabling selective delivery of hydrogen to the alkene from the same face as the directing group. The heterogeneous catalysts were observed to have conversions of 99% with a diastereomeric ratio (dr) of up to 16:1 (FIG. 1B).

The heterogeneous catalysts may be prepared by various methods. As a nonlimiting example, a fabrication method may include synthesizing bimetallic nanoparticles on a support material by co-impregnation of metal precursor salts of the noble metal and the first-row transition metal in a ratio of about 3:1 on the support material. As a particular but nonlimiting example in which the bimetallic nanoparticles are a Pd—Cu alloy, a Pd:Cu ratio of 3:1 can be obtained through co-impregnation of suitable metal precursor salts (e.g., palladium(II) nitrate hydrate (37.0-42.0% Pd), copper (II) nitrate hemi(pentahydrate) (98%)) on supporting materials (as nonlimiting examples, support materials containing or consisting entirely of Al$_2$O$_3$, SiO$_2$, CaCO$_3$, BaSO$_4$, TiO$_2$, carbon black, etc.) followed by high temperature reduction to form a heterogeneous catalyst comprising the Pd—Cu bimetallic nanoparticles (e.g., Pd$_3$Cu/Al$_2$O$_3$, Pd$_3$Cu/SiO$_2$, etc.). The diastereoselectivity of the heterogeneous catalysts may be adjusted by modifying the processing steps of the high temperature reduction process and the compositions of the bimetallic alloy nanoparticles. As such, methods for controlling the diastereoselectivity of such heterogeneous catalysts will be evident in view of the experimental results discussed below. In general, suitable reduction processes may include annealing at temperatures of about 600 to 800° C. in a reducing atmosphere (for example, H$_2$), 600 to 800° C. in an inert atmosphere (for example, N$_2$), or 600 to 800° C. in an inert atmosphere (for example, N$_2$) followed by 400 to 800° C. in a reducing atmosphere (for example, H$_2$) referred to as N$_2$/H$_2$. Nonlimiting embodiments include bimetallic nanoparticles annealed under the above-noted H$_2$/N$_2$ conditions, with further embodiments including bimetallic nanoparticles annealed under 600 to 800° C. in 5% N$_2$ followed by about 400° C. in 5% H$_2$, and still further embodiments including bimetallic nanoparticles annealed under about 800° C. in 5% N$_2$ followed by 400° C. in 5% H$_2$.

Figure 13:
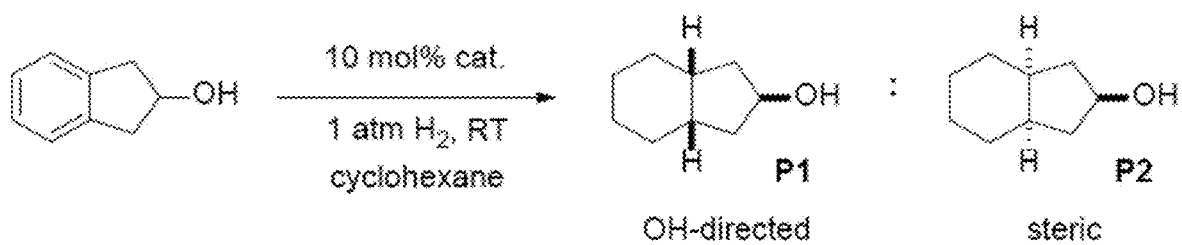
FIG. 13 includes a Table 7 that includes data related to screening of Rh-M heterogeneous catalysts for directed hydrogenation of arene substrates.

The heterogeneous catalysts may be used for directed hydrogenation of various substrates, including organic compounds that include alkenes or arenes such as but not limited to those listed in Table 4 of FIG. 9 and Table 7 of FIG. 13.

Nonlimiting embodiments of the invention will now be described in reference to experimental investigations leading up to the invention.

Various heterogeneous catalysts were prepared comprising Pd-M bimetallic nanoparticles supported by Al$_2$O$_3$ for experimental comparison with Pd:M ratios of 3:1, where M represents a first-row transition metal of Fe, Co, Ni, Cu, or Zn. An incipient wetness impregnation process was used to prepare the heterogeneous catalysts. The process included dissolving palladium nitrate hydrate and a metal nitrate hydrate of the first-row transition metal in nanopure water. The solution was added dropwise, with vigorous mixing between each addition, to aluminum oxide. The resulting powder was then dried and calcined. The calcined powder was then reduced under a flow of 5% H$_2$/95% N$_2$. In addition, a pure Pd/Al$_2$O$_3$ heterogeneous catalyst was prepared in which only the palladium nitrate hydrate was impregnated.

The resulting Pd$_3$M/Al$_2$O$_3$ heterogeneous catalysts were screened in hydrogenation of a model substrate, terpinen-4-ol, in cyclohexane under balloon pressure of H$_2$ at room temperature (Table 1 of FIG. 2). Well-ordered bimetallic surfaces with directing capability were expected to favor product P1 (see reaction above Table 1 of FIG. 2), while no significant steric preference for P2 was expected in the absence of a directing effect.

Using the pure Pd/Al$_2$O$_3$ heterogeneous catalyst, complete conversion of the substrate was observed after two hours with a diastereomeric ratio for P1/P2 (dr) of 1:1, revealing that pure Pd nanoparticles were incapable of binding the hydroxyl directing group, in line with previous reports on Pd/C heterogeneous catalysts (Table 1 of FIG. 2, entry 1). The same experiment was performed with Pd$_3$Fe/Al$_2$O$_3$, Pd$_3$Co/Al$_2$O$_3$, and Pd$_3$Ni/Al$_2$O$_3$ heterogeneous catalysts which showed conversions similar to pure Pd with slight increases in dr of about 2:1 to 3:1 toward the directed product (Table 1 of FIG. 2, entries 2 through 4). However, incomplete alloying and phase segregation of the two metals was observed, which resulted in low directivity. Performing this experiment on certain bimetallic alloys, Pd$_3$Cu/Al$_2$O$_3$ and Pd$_3$Zn/Al$_2$O$_3$, showed suppressed conversion and elevated diastereoselectivity relative to monometallic Pd, suggesting that a larger proportion of the heterogeneous catalysts formed a bimetallic structure (Table 1 of FIG. 2, entries 5 and 6). In this initial screening experiment, the Pd$_3$Cu/Al$_2$O$_3$ heterogeneous catalyst showed the highest diastereoselectivity for the directed hydrogenation with a 5:1 dr at 43% conversion in two hours. A control sample containing only Cu showed no conversion under these conditions.

Figure 3:
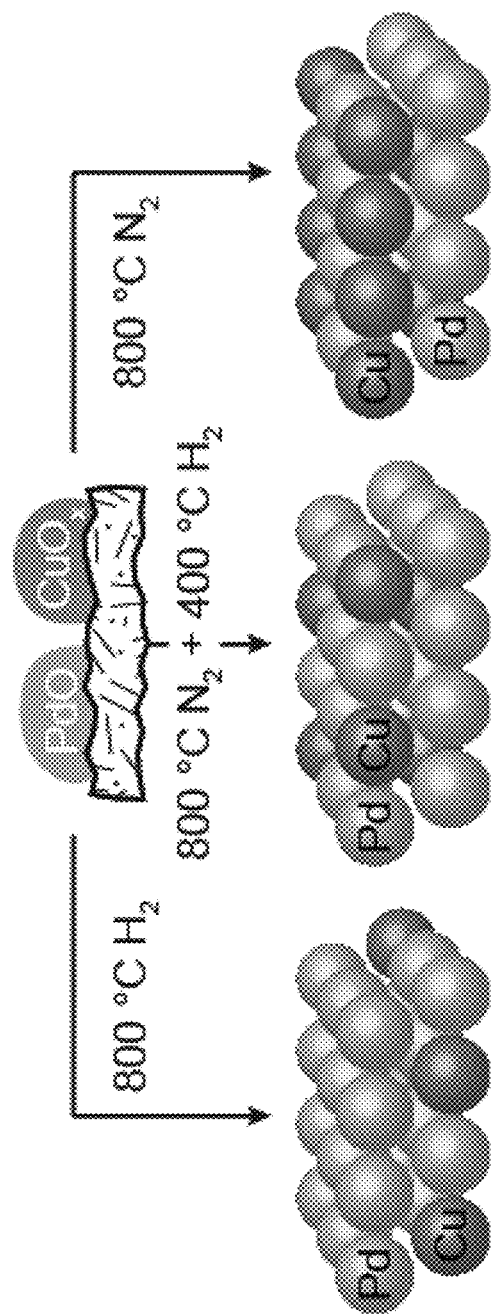
FIG. 3 schematically represents changes in Pd—Cu surface speciation as a function of thermal treatments with varying atmosphere, temperature, and sequence.

It was theorized that modifying the surface composition of the Pd—Cu alloy nanoparticles may improve selectivity toward the directed hydrogenation. Pd—Cu alloys have been known to show dynamic surface reconstruction during thermal annealing depending on the gas atmosphere and temperature regime. Pd atoms tend to preferentially migrate to the surface in the presence of strongly adsorbing gases such as H$_2$ and CO while Cu tends to segregate to the surface under high-temperature inert gas or vacuum conditions (FIG. 3). Therefore, a variety of thermal annealing steps were performed under both reducing and inert atmospheres to determine methods of controlling the surface composition of the Pd—Cu alloy nanoparticles.

Mesoporous SiO$_2$ was chosen as the support for thermal annealing studies due to superior uniformity and low polydispersity of its supported nanoparticles. For the following thermal treatments, the Pd$_3$Cu/SiO$_2$ heterogeneous catalysts were each prepared with an identical impregnated and calcined material with a 75:25 Pd/Cu ratio on SiO$_2$. The impregnation was carried out sequentially using metal ammonia precursors added to silica. The impregnated silica was dried and subsequently calcined. After calcination, only oxidized Pd and Cu species were observed. H$_2$ reduction was first performed on the calcined samples at temperatures ranging from room temperature to 800° C. (Table 1 of FIG. 2, entries 7 through 9). Since only Pd precursors can be reduced by H$_2$ at room temperature, a heterogeneous catalyst generated at room temperature comprised reduced Pd nanoparticles interspersed with Cu oxides (RT H$_2$), which showed substantially identical reactivity and selectivity to pure Pd. Catalyst selectivity increases slightly with increasing reduction temperature due to Pd—Cu alloy formation (600H$_2$). However, at best, heterogeneous catalysts treated with H$_2$ alone were observed to only achieve modest directivity (3:1 dr) and full conversion over twenty hours, consistent with formation of a Pd-rich alloy surface in the high temperature H$_2$ environment (800H$_2$).

To generate a more Cu-rich surface, the calcined sample was annealed in an inert atmosphere (N$_2$) at temperatures between 600 and 800° C. (Table 1 of FIG. 2, entries 10 through 12). Due to the lack of an external reductant, higher temperatures were required to reduce the Cu precursors and form the bimetallic alloy using only residual ammonia in the calcined material. At 600° C. under N$_2$, the heterogeneous catalyst showed high conversion and low directivity due to negligible Cu precursor reduction at this temperature (600N$_2$). As the N$_2$ annealing temperature was raised to 700 and 800° C., the diastereoselectivity rose dramatically to 10:1 and 17:1 dr, respectively, while the conversion dropped to 66% and 30% (700N$_2$, 800N$_2$), respectively.

The heterogeneous catalysts were then annealed at 400° C. in a reducing atmosphere (H$_2$) in order to more efficiently reduce and incorporate the Cu atoms into the alloy nanoparticle (Table 1 of FIG. 2, entries 13 through 15). In all tested cases, the reactivity increased while the diastereoselectivity of the N$_2$-treated heterogeneous catalyst was retained. The most selective and active heterogeneous catalyst identified, 800N$_2$-400H$_2$, achieved 16:1 dr and full conversion over twenty hours. However, raising the reduction temperature up to 800° C. after N$_2$ annealing (800N$_2$-800H$_2$) eroded the dr back down to 6:1 due to segregation of Pd to the surface. On the basis of these data, the preferred heterogeneous catalyst for both high diastereoselectivity and high conversion in this system was generated by sequential 800N$_2$-400H$_2$ treatment in order to obtain a balanced distribution of Pd and Cu on the bimetallic surface.

Figures 5A, 5B:
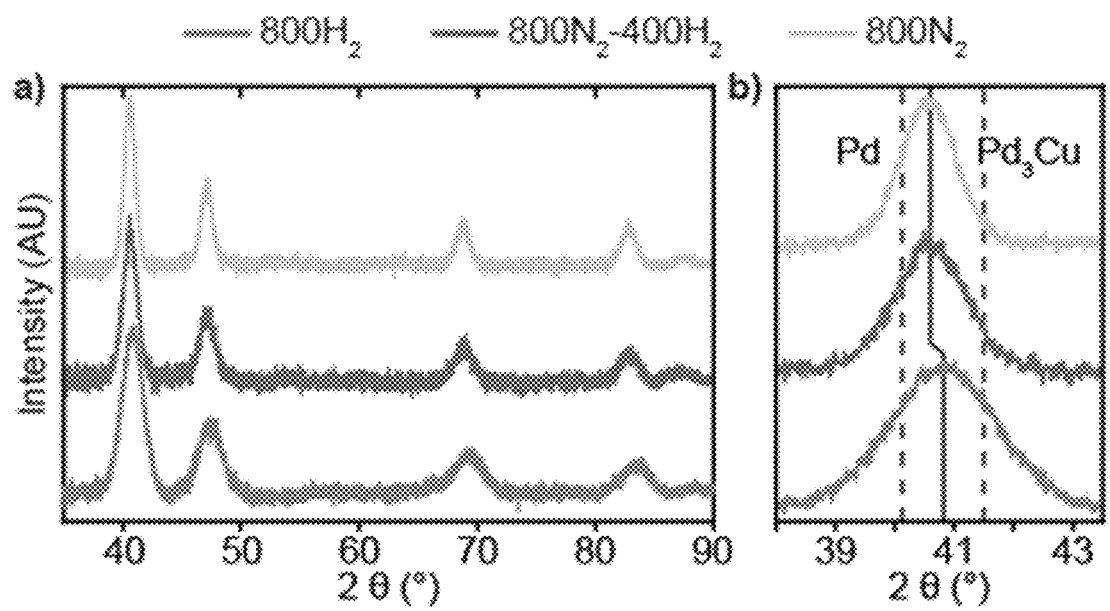
FIGS. 5A through 5D include plots representing powder XRD (FIG. 5A), close-up of XRD (111) peak (FIG. 5B), Pd K-edge EXAFS (FIG. 5C), and Cu K-edge EXAFS for $Pd_3Cu/SiO_2$ heterogeneous catalysts (FIG. 5D).

To understand the structural requirements for efficient substrate-directed hydrogenation, three Pd$_3$Cu/SiO$_2$ samples were characterized that showed distinct selectivity and conversion behavior: 800H$_2$, 800N$_2$-400H$_2$, and 800N$_2$. All tested heterogeneous catalysts showed similar nanoparticle morphology and Pd—Cu average elemental composition based on scanning-transmission electron microscopy (STEM), energy-dispersive X-ray spectroscopy (EDS), and X-ray fluorescence (XRF; FIGS. 4A-4F). Powder X-ray diffraction (XRD) showed that all samples possessed a face-centered cubic (FCC) crystal structure as expected for a solid-solution Pd—Cu alloy, and all peaks were shifted to a higher 2θ relative to a pure Pd phase (FIGS. 5A and 5B). The sample directly reduced in 5% H$_2$ (800H$_2$) showed a larger peak shift compared to those annealed first under N$_2$. The 800H$_2$ sample was calculated to have a lattice parameter of about 3.833 Å which indicated an approximate Pd$_{79}$Cu$_{21}$ structure while the 800N$_2$ and 800N$_2$-400H$_2$ samples were calculated to have lattice parameters of about 3.854 Å which indicated an approximate Pd$_{87}$Cu$_{13}$ structure.

Figures 5C, 5D:
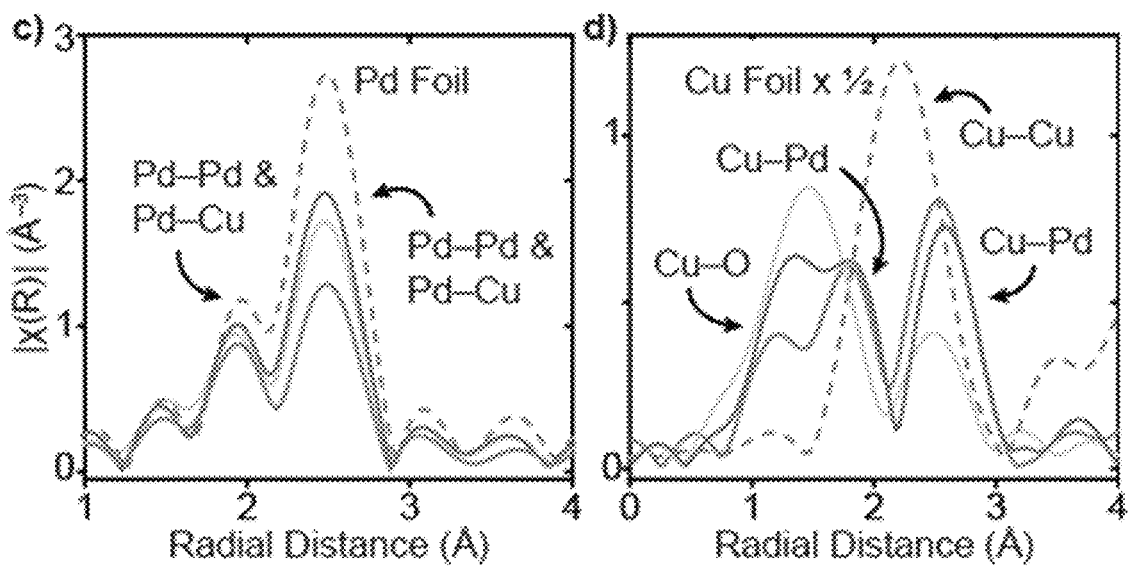

X-ray absorption fine structure (EXAFS) at the Pd K-edge showed that all samples possessed the characteristic two-peak shape of the FCC crystal structure (FIG. 5C). Fitting the EXAFS spectrum allowed for determination of the coordination numbers (CN) and bond distances (R) for all atoms within the first coordination sphere (Table 2 of FIG. 6). Consistent with XRD, EXAFS indicated that the largest amount of Pd—Cu alloying was observed in the 800H$_2$ sample followed by the 800N$_2$-400H$_2$ and 800N$_2$ samples based on the ratio of Pd—Pd to Pd—Cu CN. The 800N$_2$ sample also showed residual Pd—O scattering due to incomplete reduction of Pd precursors. At the Cu K-edge, all samples showed significant unreduced Cu—O scattering in addition to Cu—Pd scattering (FIG. 5D). The ratio of Cu—Pd to Cu—O CN in each sample paralleled the degree of alloying observed at the Pd K-edge and in the XRD pattern (Table 2 of FIG. 6). On the basis of these data, it was concluded that the bulk Pd—Cu alloy structure surprisingly did not dictate catalyst diastereoselectivity. In fact, the heterogeneous catalyst with the highest degree of bulk alloying, 800H$_2$, showed the lowest directed hydrogenation selectivity, corroborating the previously noted hypothesis that the surface composition must vary based on the thermal treatment sequence and environment.

The scattering amplitude in the Pd K-edge EXAFS spectrum, which reflects the total first-shell coordination around Pd atoms, provided indirect information about the enrichment of Pd atoms on the surface or in the core of the nanoparticle (FIG. 5C, Table 2 of FIG. 6). The low directivity 800H$_2$ heterogeneous catalyst had the lowest EXAFS scattering intensity and a total Pd-M CN of 8.6, significantly lower than the expected CN of 12 for bulk Pd atoms in an FCC structure and characteristic of Pd enrichment at the surface of the nanoparticle. In contrast, the strongly directing 800N$_2$-400H$_2$ heterogeneous catalyst had a similar average nanoparticle size but showed much higher scattering intensity and a total Pd-M CN of 11.2. Another low directivity sample (800H$_2$/Al$_2$O$_3$) was also characterized with larger average particle size compared to the SiO$_2$ samples. The 800H$_2$/Al$_2$O$_3$ sample had a total Pd-M CN of 9.4, higher than the total CN on 800H$_2$/SiO$_2$ due to the larger particles, but still in a regime that represented significant surface Pd speciation. Together with literature on Pd—Cu surface segregation, these data suggested that subtle changes to bimetallic surface composition engendered by the thermal treatments had a strong impact on directed hydrogenation behavior.

Figure 7:
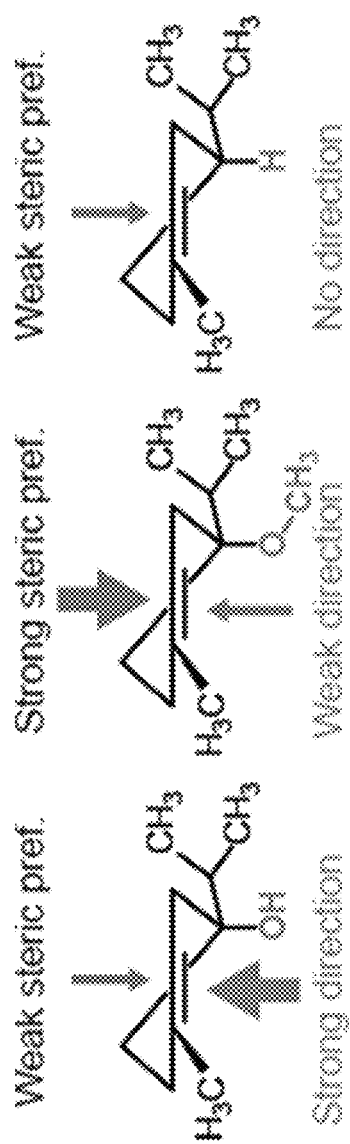
FIG. 7 schematically represents a comparison of steric versus directing selectivity preferences for different directing groups.

In order to confirm that the diastereoselectivity observed on the Pd—Cu alloy heterogeneous catalysts was in fact due to a hydroxyl directing effect, two analogues of terpinen-4-ol (R=OH) were prepared with different directing groups. Terpinen-4-ol methyl ether (R=OCH$_3$) should have had a weaker directing ability because the bulky methyl group decreases the binding affinity of the oxygen atom to the surface while p-menthene (R=H) should have exhibited no direction whatsoever (FIG. 7). When two Pd$_3$Cu/SiO$_2$ heterogeneous catalysts (800H$_2$, 800N$_2$-400H$_2$) were compared to pure Pd/SiO$_2$, it was observed that the directing effect was attenuated upon methylation or removal of the hydroxyl functional group. The methyl ether substrate had a strong steric selectivity preference due to the bulky methoxy group in the axial position, which was reflected in the 1:7 dr (P1/P2) on pure Pd (Table 3 of FIG. 8). While there was an increase in dr toward the directed product from 1:7 to 1:4 and 1:2 using Pd—Cu heterogeneous catalysts, the weak direction could never overcome the steric preference. When no directing group was present (R=H), no change in diastereoselectivity was observed between the monometallic Pd and Pd—Cu heterogeneous catalysts. The hydrogenated product exhibited a dr of about 1:3 on all tested heterogeneous catalysts due to the inherent steric preference of the substrate, illustrating that the geometric and electronic changes to the heterogeneous catalyst surface that accompany alloy formation did not affect diastereoselectivity in the absence of a directing group. The rates of reaction should also have been sensitive to the strength of directing group binding to the surface, which was observed on both Pd—Cu alloy heterogeneous catalysts. The nondirecting R=H substrate showed lower reactivity by a factor of 3 and 6 relative to R=OH and OMe substrates, respectively, because no oxygen functionality was present to facilitate substrate adsorption onto Cu surface atoms.

A few additional substrates were also evaluated to identify features that enable highly diastereoselective heterogeneous directed hydrogenation (Table 4 of FIG. 9). Both homoallylic (entries 1 and 2) and allylic alcohols (entries 3 through 8) were capable of directing the diastereoselective hydrogen addition, provided at least one additional substituent besides the OH group was present on the cyclohexene ring to reduce conformational flexibility. In particular, substrates in which the OH directing group preferred an axial position in the half-chair conformation resulted in the highest diastereoselectivities (entries 1, 2, 3, and 6). Substrates wherein the directing group preferred an equatorial position or had no conformational preference (entries 4, 5, 7, and 8) showed weaker directing effects but still noticeable increases in diastereomeric ratio relative to the pure Pd/SiO$_2$ control.

Figure 10:
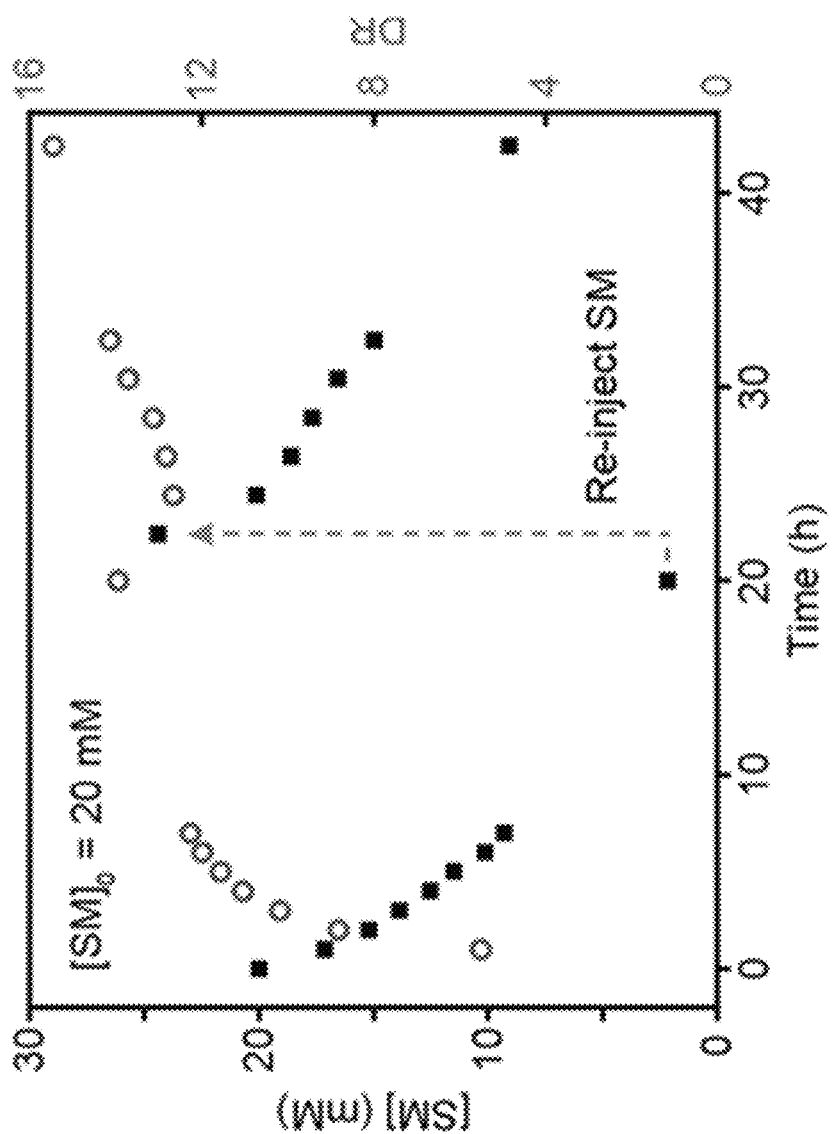
FIG. 10 includes a plot representing a starting material (terpinen-4-ol) concentration and product diastereomeric ratio versus time over a fresh Pd$_3$Cu/SiO$_2$ heterogeneous catalyst and after reinjection of a second aliquot of the starting material.

Kinetics and reusability studies were performed on the 800N$_2$-400H$_2$ Pd$_3$Cu/SiO$_2$ heterogeneous catalyst to understand surface structural evolution and heterogeneous catalyst stability over time. The conversion and selectivity for terpinen-4-ol hydrogenation over time were measured using a freshly prepared heterogeneous catalyst. Interestingly, the diastereoselectivity of the heterogeneous catalyst increased significantly over the first six hours of the reaction, likely due to bimetallic surface reconstruction that occurred upon exposure to the reaction medium (FIG. 10). The diastereoselectivity at the end of twenty hours of reaction reaches the expected 14:1 dr and 90% conversion. To avoid exposing the heterogeneous catalyst to air, a second aliquot of the substrate was injected directly into the flask. The reaction continued at a slightly slower rate, but the diastereomeric ratio of the new product formed was high from the outset, corroborating the fact that the heterogeneous catalyst surface reached a stable state after an initial reconstruction. If the Pd$_3$Cu/SiO$_2$ powder was instead filtered off and dried in the air, it was observed that the reactivity of the heterogeneous catalyst dropped significantly upon reuse though the diastereoselectivity remained high, indicating that the alloy surface deactivated significantly upon oxidation. Heterogeneous catalysts that had been exposed to air could be regenerated through a 200° C. H$_2$ reduction, which resulted in 72% conversion and a 12:1 dr over twenty hours.

As evidenced by the above-described experimental investigations, control over the composition of a bimetallic Pd—Cu surface through thermal annealing enables high diastereoselectivity in the hydroxyl-directed hydrogenation reaction of terpinen-4-ol and related substrates. It is believed that selective binding of the directing group to Cu surface atoms and activation of H$_2$ and the alkene on neighboring Pd surface atoms enable facially selective hydrogen addition to the alkene with a 16:1 diastereomeric ratio.

Pt bimetallic alloy heterogeneous catalysts, generated through incipient wetness impregnation (iwi) or colloidal (c) synthesis, were also found to be highly selective and reactive in the directed hydrogenation of terpinen-4-ol. Screening of iwi-Pt-M alloy compositions (where M is a first-row transition metal) showed that the Pt—Cu and Pt—Co alloys were capable of achieving the highest diastereoselectivities (Table 5 of FIG. 11). In the colloidally-synthesized c-Pt—Cu alloys, product diastereoselectivity was observed to increase as the fraction of Cu increased in the bimetallic structure. The highest dr of 13:1 toward the directed product was observed using Cu-rich c-PtCu$_2$ alloy nanoparticles supported on Al$_2$O$_3$.

Figure 12:
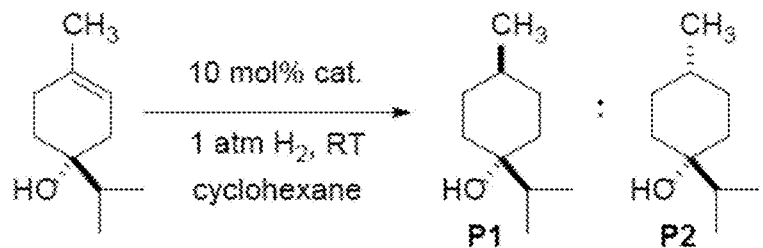
FIG. 12 includes a Table 6 that includes data related to screening of Rh-M heterogeneous catalysts for directed hydrogenation of alkene substrates.
Figure 14A:
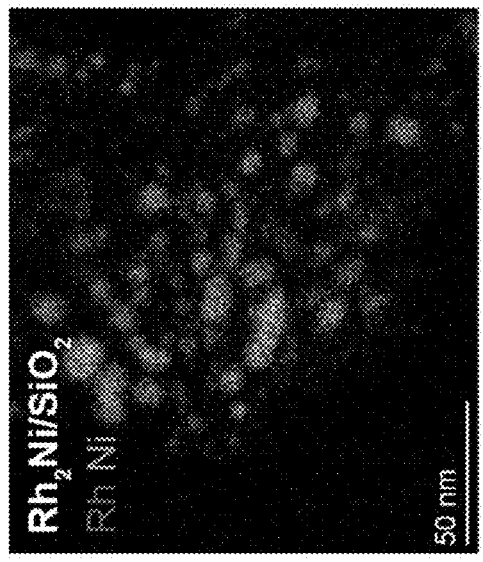
FIG. 14A through 14C include TEM and STEM-EDS maps for Rh-M alloy heterogeneous catalysts.
Figure 14B:
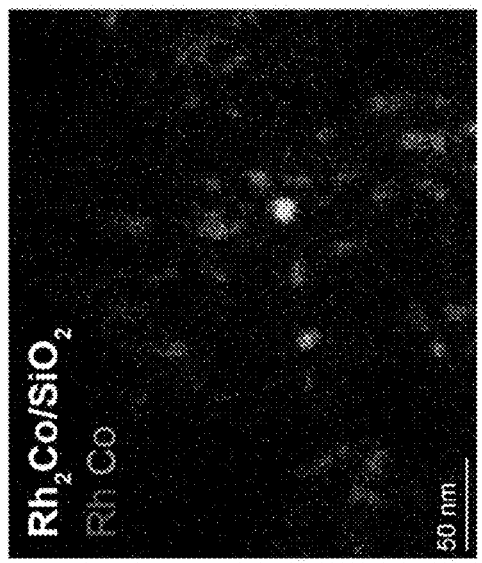

A screen of Rh alloys with the first-row transition metals Fe, Co, Ni, Cu, and Zn in terpinen-4-ol hydrogenation also showed significant diastereoinduction when a uniform M$_1$-M$_2$ alloy was formed during the high-temperature reduction step (Table 6 of FIG. 12). The Rh$_2$Ni and Rh$_2$Cu alloys showed the highest diastereoselectivities of 9:1 and 12:1, respectively, likely due to fairly uniform alloying across the sample (FIG. 14A). In contrast, the Rh$_2$Co alloy showed significant segregation of the two metals, resulting in only modest dr of 6:1 (FIG. 14B).

Figure 14C:
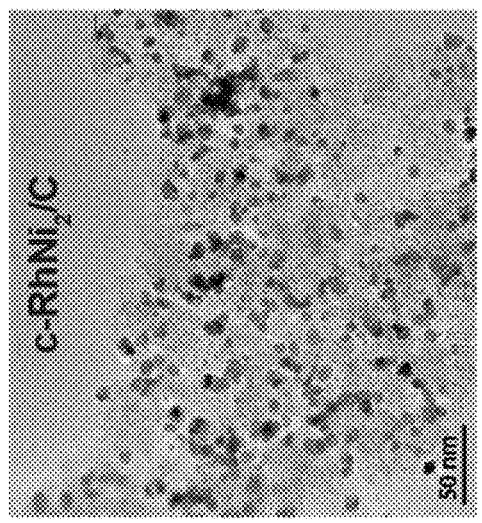

Finally, the Rh alloys were also studied in hydroxyl-directed arene hydrogenations using 2-indanol as a model substrate. Preliminary results indicate that Rh-M bimetallic alloys are capable of directing the facially-selective arene hydrogenation with dr of up to 5:1 (Table 7 of FIG. 13).
Rh—Ni alloys proved to be the most selective, and both colloidal and incipient wetness impregnation methods were applied toward the synthesis of the heterogeneous catalyst (FIG. 14C).

While the invention has been described in terms of specific embodiments, it is apparent that other forms could be adopted by one skilled in the art. For example, the surface composition of the catalyst could differ from that shown, and materials and processes/methods other than those noted could be used. Therefore, the scope of the invention is to be limited only by the following claims.

The invention claimed is:

1. A heterogeneous catalyst that is configured for directed hydrogenation of a substrate, the heterogeneous catalyst comprising bimetallic nanoparticles of $M_1$-$M_2$, wherein Mi is a noble metal and $M_2$ is a first-row transition metal, the bimetallic nanoparticles are disposed on a support material, the bimetallic nanoparticles have a bimetallic surface, and atoms of both the noble metal and the first-row transition metal have a balanced distribution across the bimetallic surfaces of the bimetallic nanoparticles.

2. The heterogeneous catalyst of claim 1, wherein the noble metal is chosen from the group consisting of Pd, Pt, and Rh.

3. The heterogeneous catalyst of claim 1, wherein the first-row transition metal is chosen from the group consisting of Fe, Co, Ni, Cu, and Zn.

4. The heterogeneous catalyst of claim 1, wherein the bimetallic nanoparticles are chosen from the group consisting of Pd-Cu, Pt-Cu, Pt-Co, Rh-Ni, and Rh-Cu alloys.

5. The heterogeneous catalyst of claim 4, wherein the support material comprises an oxide chosen from the group consisting of $SiO_2$ and $Al_2O_3$.

6. The heterogeneous catalyst of claim 1, wherein the support material comprises an oxide chosen from the group consisting of $SiO_2$ and $Al_2O_3$.

7. The heterogeneous catalyst of claim 1, wherein the substrate includes an alkene or an arene.

8. The heterogeneous catalyst of claim 1, wherein the heterogeneous catalyst is capable of hydroxyl-directed hydrogenation reaction of terpinen-4-ol with a diastereomeric ratio (dr) of greater than 6:1.

9. A method of producing a heterogeneous catalyst configured for directed hydrogenation of a substrate, the method comprising:

providing bimetallic nanoparticles disposed on a support material to produce an intermediate composition, the bimetallic nanoparticles being $M_1$-M2 wherein Mi is a noble metal and M2 is a first-row transition metal; and performing a reduction process on the intermediate composition such that atoms of both the noble metal and the first-row transition metal have a balanced distribution are distributed across the bimetallic surfaces of the bimetallic nanoparticles and thereby form the heterogeneous catalyst.

10. The method of claim 9, wherein the noble metal is chosen from the group consisting of Pd, Pt, and Rh.

11. The method of claim 9, wherein the first-row transition metal is chosen from the group consisting of Fe, Co, Ni, Cu, and Zn.

12. The method of claim 9, wherein the bimetallic nanoparticles are chosen from the group consisting of Pd-Cu, Pt-Cu, Pt-Co, Rh-Ni, and Rh-Cu alloys.

13. The method of claim 12, wherein the support material comprises an oxide chosen from the group consisting of $SiO_2$ and $Al_2O_3$.

14. The method of claim 9, wherein the support material comprises an oxide chosen from the group consisting of $SiO_2$ and $Al_2O_3$.

15. The method of claim 9, further comprising producing the bimetallic nanoparticles on the support material by co-impregnation of metal precursor salts of the noble metal and the first-row transition metal in a ratio of 3:1 on the support material.

16. The method of claim 9, wherein the reduction process comprises a thermal treatment in inert atmosphere at about 600° C. to about 800° C. or a thermal treatment in a reducing atmosphere at about 400 to 800° C.

17. The method of claim 9, wherein the reduction process comprises annealing in an inert atmosphere at about 600° C. to about 800° C., and then reducing in a reducing atmosphere at about 400 to 800° C.

18. The method of claim 9, wherein the reduction process comprises annealing in an inert atmosphere at about 600° C. to about 800° C., and then reducing in a reducing atmosphere at about 400° C.

19. The method of claim 9, wherein the reduction process comprises annealing in an inert atmosphere at about 800° C., and then reducing in a reducing atmosphere at about 400° C.

20. The method of claim 9, further comprising performing with the heterogeneous catalyst directed hydrogenation of a substrate that includes an alkene or an arene.

* * * * *